United States Patent [19]

Schöner

[11] Patent Number: 5,468,221
[45] Date of Patent: Nov. 21, 1995

[54] IMPLANTABLE CATHETER MADE OF HIGH COLD FLOW MATERIAL

[76] Inventor: Wolfgang Schöner, Hainholzweg 20, 3400 Gottingen, Germany

[21] Appl. No.: 262,367

[22] Filed: Jun. 20, 1994

Related U.S. Application Data

[63] Continuation of Ser. No. 838,266, filed as PCT/EP90/01537, Sept. 12, 1990, abandoned.

[30] Foreign Application Priority Data

Sep. 14, 1989 [DE] Germany .................... 39 30 770.0

[51] Int. Cl.$^6$ ..................................... A61M 5/00
[52] U.S. Cl. .............. 604/8; 604/264; 604/280; 138/137
[58] Field of Search ................. 138/125, 137, 138/140; 604/280, 264, 282, 8; 623/1, 11, 12

[56] References Cited

U.S. PATENT DOCUMENTS

| | | | |
|---|---|---|---|
| 3,334,165 | 8/1967 | Koch ........................................ | 138/125 |
| 3,561,493 | 2/1971 | Maillard et al. ......................... | 138/137 |
| 3,623,484 | 11/1971 | Schulte . | |
| 3,638,649 | 2/1972 | Ersek ........................................ | 604/8 |
| 4,211,741 | 7/1980 | Ostoich . | |
| 4,254,180 | 3/1981 | Kline ........................................ | 623/1 |
| 4,282,876 | 8/1981 | Flynn . | |
| 4,424,305 | 1/1984 | Gould et al. ............................. | 623/11 |
| 4,619,641 | 10/1986 | Schanzer ................................. | 604/8 |
| 4,627,844 | 12/1986 | Schmitt . | |
| 4,731,073 | 3/1988 | Robinson ................................ | 623/1 |
| 4,737,153 | 4/1988 | Shimamura et al. .................... | 604/282 |
| 4,791,965 | 12/1988 | Wynn ....................................... | 138/137 |
| 4,994,047 | 2/1991 | Walker et al. ........................... | 604/265 |

OTHER PUBLICATIONS

"HIGHLIGHTS: Pellethane 2363 Series", DSG Report No. 17, The Donald S. Gilmore Laboratories, The Upjohn Company.

*Primary Examiner*—C. Fred Rosenbaum
*Assistant Examiner*—Ronald K. Stright, Jr.
*Attorney, Agent, or Firm*—Oblon, Spivak, McClelland, Maier & Neustadt

[57] ABSTRACT

Implantable catheter made of medically tolerated synthetic material, whose thermoplastic polymer has an excellent cold flow at 34° C. to 40° C. under a weight load of 40 g/0.2 mm$^2$, so that, in the case of a continuous tensile load for 63 days, the initial length of the catheter increases by at least 50% in the direction of the longitudinal axis, the extruded catheter tube consisting of three layers connected to each other and arranged coaxially, and the middle layer containing a radiopaque pigment.

14 Claims, No Drawings

IMPLANTABLE CATHETER MADE OF HIGH COLD FLOW MATERIAL

This application is a continuation of application Ser. No. 07/838,266, filed Mar. 12, 1992, abandoned, which was filed as International Application No. PCT/EP90/01537 on Sep. 12, 1990.

BACKGROUND OF THE INVENTION

1. Field of the Invention

The invention relates to an implantable catheter made of medically tolerated synthetic material, containing an elastic, plastically deformable polymer having a particularly high cold flow.

2. Discussion of the Background

U.S. Pat. No. 4,211,741 describes a coextruded medical-surgical tubing. The polyurethane layer (innen layer) creates a non-migrating medical-surgical inner surface, and the polyvinyl layer creates an inexpensive outer surface. The relative thickness of the two layers are selected to provide the desired characteristics, such as hardness, flexibility, coupler adaptability and the like.

DE-A-2,902,434 discloses a method for the deformation of vessel implants and for the preparation of tissue incorporation, in particular of umbilical cords. For the purpose of deformation, the umbilical cord is first dehydrated and then treated with an aldehyde. In order to facilitate the incorporation of the implant, the surface is roughened mechanically.

DE-A-3,239,318 deals with a formable polyurethane elastomer which has good blood tolerability and which is the product of reaction of an aliphatic organic diisocyanate, a polyether polyol of high molecular weight and 1,4-butanediol as a chain lengthener. By using two equivalents of diisocyanate per equivalent of the polyol of high molecular weight, an elastomeric material with a Shore A hardness of 70 is obtained. The polyurethane can be used for catheters.

In the DSG Report No. 17 of January 1984 (The Donalds Gilmore Laboratories) on Pellethane 2363, polyether/polyurethane resins which comply with the FDA requirements are described for medical purposes. The starting materials used are polytetramethylene ether glycol, 1,4-butanediol and diphenylmethane diisocyanate. The polyurethane can be made radiopaque by adding materials such as $BaSO_4$. Despite the biological tolerability, express reference is made to the fact that, on account of the lack of long-term data, use for implants is not recommended.

The purpose of the known biologically tolerated substances was to produce continuously elastic, thermoplastic polymers which are dimensionally stable.

One disadvantage of known implantable catheters made of medically tolerated synthetic materials consists in the fact that their length in the implanted state is virtually constant. There are cases, however, when changes in the size of the body of the patient, for example growth, results in a failure of the implanted tube system or of the catheter, because the catheter does not grow too and the implanted lumen connection necessary for maintaining the body functions is broken. Thus, it is necessary, for example in the case of neonates or infants with disorders of the cerebrospinal fluid circulation in the cranial region, to drain excess fluid from the ventricle chamber system by means of a catheter, for example into the peritoneal cavity. Since disorders of this type cannot at present be rectified other than by implanting a catheter, the growth of the body with increasing age has the result that an implanted catheter becomes too short and the drainage or feeding of fluid from or, respectively, to certain areas of the body is impaired or interrupted. Since replacement of catheters which may be too short cannot in most cases be carried out in good time, the failure of the artificial lumen connections inside the body often has serious consequences on the patient's health.

SUMMARY OF THE INVENTION

The aim of the invention is to produce a catheter whose length in the implanted state increases in line with the growth of the body, so that a permanent functioning of the lumen connection produced in the body by means of the catheter is ensured.

This object is achieved by means of an implantable extruded catheter, having coextruded layers, connected to each other and arranged coaxially made of medically tolerated, elastic, plastically deformable synthetic material, characterized in that the extruded catheter tube consists of three layers of one polymer or a mixture of polymers, whose cold flow at 34° C. to 40° C. under a weight load of 40 $g/0.2\ mm^2$ for 63 days results in an increase in the initial length of at least 50% in the direction of the longitudinal axis. The middle layer contains a radiopaque pigment, and the smooth outer surface of the catheter tube is slightly roughened at one end and at a distance from the other end over a length of approximately 5 mm.

DETAILED DESCRIPTION OF THE PREFERRED EMBODIMENTS

The so-called cold flow is understood as the flow of a polymer material under pressure or tensile load at temperatures below the glass transition temperature of the polymer. Cold flow is regarded by specialists as a frequently undesired property of polymer materials, which property, however, can be diminished, but not completely suppressed, in the case of relatively soft polymers by appropriate selection of the monomers, certain polymerization conditions and, where appropriate, crosslinking. Cold flow is a measurement of the plastic, irreversible deformability of the polymer in the region of room temperature. The Shore hardness and modulus of elasticity are measurements of the elastic behaviour of polymers, but they do not permit any conclusions to be made as regards the irreversible plastic deformability below the glass transition temperature.

It has been found, very surprisingly, that cold flow—this property of polymers which has hitherto been regarded by most specialists as a disadvantage—can be used to achieve the aim according to the invention if, for implantable catheters, a medically tolerated elastic, plastically deformable polymer is chosen which has an excellent cold flow. The so-called cold flow should, in the case of a permanent weight load (tensile load) on the catheter tube in the longitudinal direction of 40 $g/0.2\ mm^2$ cross-sectional surface of the polymer material, increase the initial length by at least 50% in 63 days, without thereby causing any damage to the catheter tube. In order to permit the incorporation of the catheter according to the invention at the desired sites, it has proven expedient to slightly roughen the outer surface of the catheter tube, which is produced smooth by means of extrusion, in order to promote the attachment of fibroblasts following implantation. This leads to an incorporation of the catheter in the tissue, so that the catheter is fixed at the incorporated sites. If, as a result of a change in the size of the patient's body, the distance between the fixation points of the catheter tube now changes, the latter becomes subject to tensile stress. As a result of the excellent cold flow of the polymer, the tensile stress decreases again as the catheter lengthens. The cold flow permits an appropriate increase in the length of the implanted catheter tube between the fixation points inside the body.

Suitable for the catheter according to the invention are relatively soft, plastically deformable polymers, which should be neither hydrolysable nor degradable fermentatively/enzymatically. Suitable medically tolerated polymers are thermoplastics, such as aliphatic polyetherurethanes, polyamides, low-density polyethylene (LDPE), polypropylene and mixtures thereof.

The polymers may be both homopolymers as well as copolymers which are sufficiently resistant to hydrolysis. Aliphatic polyetherurethanes from polyalkylene glycol ethers and suitable organic aliphatic diisocyanates, such as diphenylmethane-4,4-diisocyanate, which may optionally be loosely crosslinked with 1,4-butanediol, are preferred. In order to obtain a sufficiently soft, plastically deformable polyurethane, it is necessary, for the reaction between the diol and the polyisocyanate, to use more than two equivalents of polyisocyanate per equivalent of diol. A polyisocyanate:diol equivalence ratio of >2 to 6 is preferred.

A very particularly preferred polyalkylene glycol is polytetramethylene ether glycol of the formula $HO(CH_2CH_2CH_2CH_2O)_nH$, in which n is an integer of 2 or more. However, other polyether alcohols can also be used for the reaction with diisocyanates to produce loosely crosslinked polyurethanes with the excellent cold flow. The reaction of 1,4-butanediol and other diols with suitable aliphatic diisocyanates to give linear, elastic polyurethanes with good hydrolysis resistance and the desired plastic deformability and the necessary cold flow poses no problems to the person skilled in the art. As regards the polyamides, those types with low crystallization are particularly suitable for the catheters according to the invention.

In order to facilitate the implantation and the correct positioning of the catheters according to the invention, the polymer is provided with a radiopaque material before extrusion of the catheter tube. Suitable radiopaque materials are, for example, $BaSO_4$, bismuth compounds, tungsten or tungsten compounds, tantalum powder or noble metals in very fine distribution. The radiopaque material portion can amount to between 1% by weight and 20% by weight relative to the total weight of the polymer provided with filler. In order to facilitate the extrusion and to stabilize this long-term, auxiliaries such as stabilizers and other medically tolerated auxiliaries can be added to the polymers during processing.

In order to prevent interactions between the radiopaque material and the tissue following implantation, the polymer made radiopaque is provided on the outside and the inside of the catheter tube with a protective layer of the same, or a compatible, plastically deformable polymer without radiopaque material. The coaxial arrangement of the protective layers can be produced in a particularly simple way by coextrusion through appropriate tubular dies. It is preferable to design the outer layers or protective layers thinner than the middle layer containing pigment. The multilayer design of the catheter tube has the additional advantage that the risk of breaking is reduced. The residual elasticity of the polymer, which remains in spite of the plastic deformability of the polymer, makes it possible to bend the catheter tube freely 360° with a bending diameter of 5 mm without breaking.

The catheter can be designed both as a single-lumen catheter and with several lumina. In the case of a single-lumen catheter, it is preferably to have an internal diameter of the catheter tube of 0.8 mm to 1.8 mm and a wall thickness of 0.1 mm to 0.5 mm, preferably to 0.3 mm.

The invention also includes a method for producing a catheter made of medically tolerated synthetic material by means of coextrusion, at temperatures of 150° C. to 170° C., of the polymer mixture through an appropriate die made of Teflon-coated metal, an alloy available under the name Hostalloy® for producing extrusion dies. In order to obtain an especially smooth outer surface of the catheter tube, which prevents undesired firm attachment of fibroblasts, it is preferable to cool the extrudate with cold water flowing in the laminar direction. After drying of the extruded tube, this is divided up into catheters of the desired length, and roughening can be carried out on desired areas of the outer surface. The surface is preferably slightly roughened over a length of 5 mm at one end of the catheter and at a distance from the other end by means of slightly damaging the smooth surface skin formed on extrusion.

It is also possible, on extrusion, not to completely degas the polymer for the outer layer, or else to charge it with an inert gas, in order to bring about bubble formation in the outer layer. These bubbles burst during bending of the catheter and afford a roughened surface. If imperfections of this type are produced at intervals of about 40 cm on extrusion, then catheter lengths can be cut which exhibit roughening at the desired areas. In order to permit fixation of the catheter according to the invention following implantation, the catheter is roughened at one end and is roughened either at the opposite end or, preferably, at a certain distance from the other end.

The catheters according to the invention can be used for producing artificial lumen connections inside the body.

The catheter according to the invention is particularly suitable for the treatment of internal as well as external communicating and obstructive hydrocephalus of every genesis (following intracranial haemorrhaging, following infections, in tumour diseases, intracranial space requirements, cerebrovascular disorders, stenosis of the aquaduct of the cerebrum, and in malformations) in children and adults. Furthermore the catheter can be used for the treatment of chronic intracranial as well as intraspinal and intramedullary accumulations of fluid by means of drainage into the peritoneal cavity or into the venous system or into the right heart or the right atrium of the heart.

EXAMPLE

Establishment of a Ventriculo-peritoneal Shunt using a Pressure- or Flow-controlled Valve.

A cut is made in the skin to the right or left alongside the median line (about 2 cm) directly over the coronal suture of the cranium. Immediately in front of the coronal suture, a bore 0.5 to 1.5 cm in size is made in the cranial vault and the dura mater is exposed. Following punctiform coagulation and perforation of the dura mater, a catheter with a blind end and with no sharp edges, 3.5 to 7 cm in length, with 2 to 20 lateral holes of any size, and made of the same material as the "peritoneal-atrial catheter" is advanced via the opening in the dura mater through the frontal brain into the right or left lateral ventricle, and the brain-remote end is firmly connected to the valve provided (manufacturer PS-Medical). After making a skin incision above the umbilicus over one of the two straight muscles of the abdomen, the outer muscle fascia is incised and a trocar is inserted, by means of which the peritoneal cavity is finally punctured by perforation of the visceral muscle fascia and of the peritoneum. The hollow-needle-type trocar with a cross-section of at least 3 mm is used for advancing one end of a catheter according to the invention, which is up to 90 cm in length and is made of elastic polymers (silicone elastomer from Dow Corning), into the peritoneal cavity by a maximum length of 20 cm. A lance-shaped instrument is then used to form a channel in the subcutaneous fatty tissue via a retroauricular auxiliary incision as far as the free valve support, and a suture is threaded in in such a way that a subcutaneous attachment of the catheter partially lowered into the peritoneal cavity is possible. The free head-side catheter end is connected in a non-detachable manner to the free valve support. After checking the functioning, the skin wounds are sewn up sterilized.

I claim:

1. An implantable catheter having two ends of about 5 mm in length, comprising:

an inner layer made of a medically tolerated, elastic, plastically deformable synthetic material, a middle layer coaxially arranged thereon, made of a second medically tolerated, elastic, plastically deformable synthetic material, further containing a radiopaque material, and an outer layer coaxially arranged thereon, made of a third medically tolerated, elastic, plastically deformable synthetic material, said outer layer being roughened at said ends of said implantable catheter, wherein each of said synthetic materials has a cold flow at a temperature of from 34° C. to 40° C. under a weight load of 40 g/0.2 mm$^2$ for 63 days which results in an increase in the initial length of at least 50% in the direction of the longitudinal axis, wherein the implantable catheter undergoes cold flow to increase in length in the implanted state in line with the growth of a body in which it is implanted, and wherein said synthetic materials are neither hydrolyzable nor fermentatively or enzymatically degradable.

2. The implantable catheter of claim 1, wherein each of said synthetic materials is selected from the group consisting of an aliphatic polyurethane, a polyamide, a low-density polyethylene, a polypropylene and mixtures thereof.

3. The implantable catheter of claim 2, wherein at least one of said synthetic materials is said aliphatic polyurethane, said aliphatic polyurethane being an aliphatic polyetherurethane formed from a polyalkylene glycol ether, and the remaining synthetic materials are compatible therewith.

4. The implantable catheter of claim 3, wherein said aliphatic polyetherurethane is formed from 1,4-butanediol and diphenylmethane-4,4-diisocyanate.

5. The implantable catheter of claim 1, wherein said outer layer is thinner than said middle layer.

6. The implantable catheter of claim 5, wherein said radiopaque material is in a very fine distribution.

7. The implantable catheter of claim 6, wherein said radiopaque material is selected from the group consisting of bismuth compounds, tungsten, tungsten compounds, tantalum and noble metals.

8. The implantable catheter of claim 6, wherein said radiopaque material is $BaSO_4$.

9. The implantable catheter of claim 5, wherein said inner layer is thinner than said middle layer.

10. The implantable catheter of claim 1, wherein said implantable catheter consists essentially of said inner layer, said middle layer and said outer layer.

11. The implantable catheter of claim 10, having a single lumen with an internal diameter of from 0.8 to 1.8 mm and a wall thickness of from 0.1 to 0.5 mm.

12. The implantable catheter of claim 1, having several parallel lumina.

13. The implantable catheter of claim 1, prepared by a process comprising the steps of:

coextruding said synthetic materials through a multilayer tubular die at a temperature of from 150° C. to 170° C. to prepare an extrudate having two ends, said die being made of a poly(tetrafluoroethylene)-coated alloy, cooling said extrudate with cold water, drying the cooled extrudate, and roughening the outer surface of said ends of the dried extrudate over a length of about 5 mm.

14. A method of transferring body fluid from a first body cavity to a second body cavity, comprising implanting a catheter having two ends of about 5 mm in length, said catheter comprising:

an inner layer made of a medically tolerated, elastic, plastically deformable synthetic material, a middle layer coaxially arranged thereon, made of a second medically tolerated, elastic, plastically deformable synthetic material, further containing a radiopaque material, and an outer layer coaxially arranged thereon, made of a third medically tolerated, elastic, plastically deformable synthetic material, said outer layer being roughened at said ends of said implantable catheter, wherein each of said synthetic materials has a cold flow at a temperature of from 34° C. to 40° C. under a weight load of 40 g/0.2 mm$^2$ for 63 days which results in an increase in the initial length of at least 50% in the direction of the longitudinal axis, wherein the implantable catheter undergoes cold flow to increase in length in the implanted state in line with the growth of a body in which it is implanted, and wherein said synthetic materials are neither hydrolyzable nor fermentatively or enzymatically degradable; and draining said body fluid from said first body cavity to said second body cavity.

\* \* \* \* \*